US011291677B2

(12) United States Patent
Vigsnæs et al.

(10) Patent No.: US 11,291,677 B2
(45) Date of Patent: Apr. 5, 2022

(54) SYNTHETIC COMPOSITION FOR MICROBIOTA MODULATION

(71) Applicant: Glycom A/S, Hørsholm (DK)

(72) Inventors: Louise Kristine Vigsnæs, Copenhagen (DK); Bruce McConnell, La Tour de Peilz (CH)

(73) Assignee: Glycom A/S, Hørsholm (DK)

( * ) Notice: Subject to any disclaimer, the term of this patent is extended or adjusted under 35 U.S.C. 154(b) by 50 days.

(21) Appl. No.: 16/613,082

(22) PCT Filed: May 9, 2018

(86) PCT No.: PCT/IB2018/053219
§ 371 (c)(1),
(2) Date: Nov. 12, 2019

(87) PCT Pub. No.: WO2018/207110
PCT Pub. Date: Nov. 15, 2018

(65) Prior Publication Data
US 2020/0163982 A1 May 28, 2020

(30) Foreign Application Priority Data
May 9, 2017 (DK) .......................... PA 2017 70326

(51) Int. Cl.
*A61K 31/702* (2006.01)
*A61P 1/00* (2006.01)
*A61K 9/00* (2006.01)
*A61K 35/745* (2015.01)

(52) U.S. Cl.
CPC .......... *A61K 31/702* (2013.01); *A61K 9/0053* (2013.01); *A61K 35/745* (2013.01); *A61P 1/00* (2018.01)

(58) Field of Classification Search
CPC .. A61K 31/702; A61K 35/745; A61K 9/0053; A61P 1/00
USPC .......................................................... 514/54
See application file for complete search history.

(56) References Cited

U.S. PATENT DOCUMENTS

| | | | |
|---|---|---|---|
| 2012/0171165 A1* | 7/2012 | Buck | A61P 29/00 424/93.4 |
| 2012/0294840 A1* | 11/2012 | Newburg | A61P 1/00 424/93.44 |
| 2016/0243138 A1 | 8/2016 | Hennet et al. | |
| 2016/0287619 A1 | 10/2016 | Vigsnæs et al. | |

FOREIGN PATENT DOCUMENTS

| | | |
|---|---|---|
| WO | 01/04341 A1 | 1/2001 |
| WO | 2007101862 A1 | 9/2007 |
| WO | 2010115934 A1 | 10/2010 |
| WO | 2010115935 | 10/2010 |
| WO | 2011100979 A1 | 8/2011 |
| WO | 2011100980 | 8/2011 |
| WO | 2012007588 A9 | 1/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2016138911 A1 | 9/2016 |
| WO | 2017/046711 A1 | 3/2017 |
| WO | 2017/071716 A1 | 5/2017 |
| WO | 2017071715 A1 | 5/2017 |

OTHER PUBLICATIONS

Li et al. (J Nutr. 2012:681-689).*
Ward et al. (Mol. Nutr. Food Res. 2007, 51, 1398-1405).*
Alegría et al. (Gut Pathogens 2014, 6:31, pp. 1-6).*
M. Chichlowski, et al., "Bifidobacteria isolated from infants and cultured on human milk oligosaccharides affect intestinal epithelial function", J Pediatr Gastroenterol Nutr., Sep. 2012, pp. 1-17.
Ap Allen, et al., "Bifidobacterium longum 1714 as a translational psychobiotic: modulation of stress, electrophysiology and neurocognition in healthy volunteers", Transl Psychiatry, Nov. 1, 2016, pp. 1-7.
F. Bottacini, et al., "Diversity, ecology and intestinal function of bifidobacteria", 11th International Symposium on Lactic Acid Bacteria Egmond aan Zee, the Netherlands, Aug. 31-Sep. 4, 2014, pp. 1-15.
A. Kindworth et al., Evaluation of general 16S ribosomal RNA gene PCR primers for classical and next-generation sequencing-based diversity studies, Nucleic Acids Research, 2013, vol. 41, No. 1, Aug. 28, 2012, pp. 1-11.
S. Duranti et al., "Exploration of the Genomic Diversity and Core Genome of the Bifidobacterium adolescentis Phylogenetic Group by Means of a Polyphasic Approach", Applied and Environmental Microbiology vol. 79 No. 1, Jan. 2013, pp. 336-346.
Xi Chen, "Human Milk Oligosaccharides (HMOS): Structure, Function, and Enzyme-Catalyzed Synthesis" Advances in Carbohydrate Chemistry and Biochemistry, vol. 72, 2015, pp. 113-190.
L. Bode, "Human milk oligosaccharides and their beneficial effects", Handbook of dietary and nutritional aspects of human breast milk, Human Health Handbooks No. 5, 2013, pp. 515-531.
T. Urashima et al., "Milk Oligosaccharides", Nova Biomedial Books, 2011, pp. 1-99.
R. Berni et al., Potential beneficial effects of butyrate in intestinal and extraintestinal diseases, World J Gastroenterol vol. 17, Issued 12, Mar. 28, 2011, pp. 1519-1528.
B. Strasser, "Probiotic Supplements Beneficially Affect Tryptophan-Kynurenine Metabolism and Reduce the Incidence of Upper Respiratory Tract Infections in Trained Athletes: A Randomized, Double-Blinded, Placebo-Controlled Trial", Nutrients 2016, Nov. 23, 2016, pp. 1-15.

(Continued)

*Primary Examiner* — Eric Olson
*Assistant Examiner* — Michael C Henry
(74) *Attorney, Agent, or Firm* — Kunzler Bean & Adamson

(57) ABSTRACT

The invention relates to a composition comprising one or more human milk oligosaccharides (HMOs) for use in stimulating the production of butyrate in the gastro-intestinal tract of a non-infant human and obtaining delayed increase in the level of butyrate in the gastro-intestinal tract of the non-infant human, and methods for their use.

19 Claims, 1 Drawing Sheet

(56) References Cited

OTHER PUBLICATIONS

Figure 1:
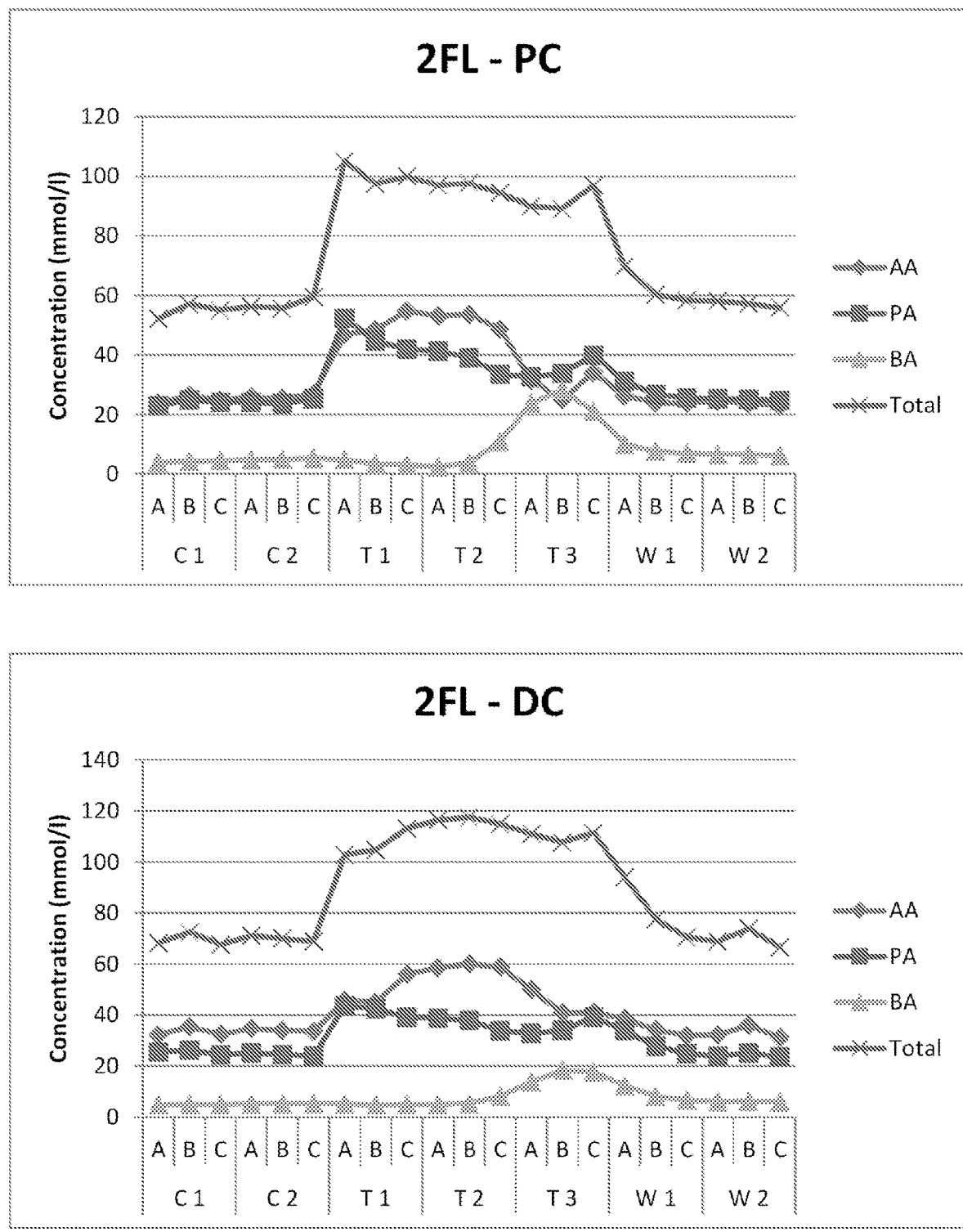

C. Schwab, et al., "Trophic Interactions of Infant Bifidobacteria and Eubacterium hallii during L-Fucose and Fucosyllactose Degradation", Frontiers in Microbiology | www.frontiersin.org, vol. 8, Artical 95, Jan. 27, pp. 1-14.

RC Edgar, "Uparse: highly accurate OTU sequences from microbial amplicon reads", Nature Methods vol. 10 No. 10, Oct. 2013, pp. 996-1000.

PCT/IB2018/053219, "International Search Report", PCT, dated Jun. 29, 2018, pp. 1-8.

PCT/IB2018/053219, "Written Opinion of the International Searching Authority", PCT, dated Jun. 29, 2018, pp. 1-10.

E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.

G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.

M. Haarman et al., Quantitative Real-Time PCR Assays To Identify and Quantify Fecal Bifidobacterium Species in Infants Receiving a Prebiotic Infant Formula, Applied and Environmental Microbiology, vol. 71, No. 5, May 2005, pp. 2318-2324.

\* cited by examiner

SYNTHETIC COMPOSITION FOR MICROBIOTA MODULATION

FIELD OF THE INVENTION

This invention relates to a method and composition for increasing the level of butyrate produced in the gastro-intestinal tract of non-infant humans.

BACKGROUND OF THE INVENTION

It has been estimated that the human intestine harbours $10^{13}$ to $10^{14}$ bacterial cells and the number of bacteria outnumbers the total number of cells in the body by a factor of 10. The microbiota of the human intestine is a complex and very dynamic microbial ecosystem, which is considered to serve numerous important functions for its human host, including protection against pathogens, induction of immune regulatory functions, nutrient processing and metabolic functions. The intestinal microbiota consists of various populations, which are important to preserve human health, and recent research has been able to link imbalances in the intestinal bacterial population to both intestinal and extra-intestinal inflammatory diseases.

Selective stimulation of specific intestinal bacteria to promote their growth and metabolic activity could be a helpful approach in creating a benign intestinal microbial community. Because some bacteria can produce a large selection of carbohydrate active enzymes (such as glycoside-hydrolases and transporters), the bacteria can grow on carbon sources, which may be less easily used by other members of the intestinal microbial community.

Human milk oligosaccharides (HMOs) are a heterogeneous mixture of soluble glycans found in human milk. They are the third most abundant solid component after lactose and lipids in human milk and are present in concentrations of 5-25 g/l (Bode, in: *Handbook of dietary and nutritional aspects of human breast milk* (Zibadi et al. eds.), 515-31, Wageningen Academic Publishers (2013)). HMOs are resistant to enzymatic hydrolysis in the small intestine and are thus largely undigested and unabsorbed. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of bifidobacteria in the gut of breast-fed infants compared to a more diverse gut microbiota in formula-fed infants. This is viewed as beneficial for the infant because strains of *Bifidobacterium* species are believed to have a positive effect on gut health (Chichlowski et al. *J. Pediatr. Gastroenterol. Nutr.* 55, 321 (2012)).

Bifidobacteria are considered one of the most beneficial probiotics. As an example, strains of *B. bifidum* and *B. longum* have been widely studied for their immunomodulatory properties and protecting effect by supressing pathogens. Species of *Bifidobacterium* grown on HMOs have been shown to down regulate expression of virulence genes from pathogenic bacteria such as *E. coli* 0157 and *Salmonella enterica* serovar *Typhimurium*, and affect epithelial cell function by regulating immune gene expression and tight junction (Chichlowski et al. *J. Pediatr. Gastroenterol. Nutr.* 55, 321 (2012)). Bifidobacteria are also able to affect the gut/brain axis; for example by impacting tryptophan (an important metabolite for the gut and brain interaction). It has been shown that *B. bifidum* combined with other probiotic bacteria can impact tryptophan levels in blood. An inverse correlation of serum levels of tryptophan with concentration of faecal calprotectin, a marker for gut permeability, has been reported in patients suffering from Alzheimer's disease, thus indicating a close relationship between the intestinal barrier function and tryptophan concentration in blood (Strasser et al. *Nutrients* 8, 752 (2016)]. Additionally, consumption of *B. longum* is associated with reduced stress and improved memory (Allen et al. *Translational Psychiatry* 6, e939 (2016)).

Metabolic end products such as short chain fatty acids (acetate, propionate and butyrate), produced during carbohydrate fermentation, also contribute to intestinal functionality and probiotic attributes of bifidobacteria. It has previously been shown that acetate produced by bifidobacteria can enhance intestinal defence mediated by epithelial cells and thereby protect the host against assault. In addition, while bifidobacteria do not produce butyrate as an end product of fermentation, the importance of metabolic cross-feeding on acetate by butyrate-producing bacteria in the gut has been demonstrated. A study has shown that the butyrate-producing species such as *E. hallii* can utilize intermediates of bifidobacterial HMO fermentation, such as acetate and lactate, and produce butyrate (Schwab et al. *Frontiers in Microbiolog*, 8, 1 (2017)). Butyrate is the primary energy source for colonocytes and has been reported to regulate the physical and functional integrity of the normal colonic mucosa by altering mucin gene and tight junction expression. Additionally, butyrate has immunomodulatory effects keeping the immune cells in balance, and can impact the expression of brain-derived neurotrophic factor and glia-derived neurotrophic factor leading to neuron regulation. Several studies have shown a protective effect of butyrate reducing the risk of disease, including irritable bowel syndrome (IBS), inflammatory bowel disease (IBD), colon cancer, liver damage and autism like behavior (Canani et al. *World J. Gastroenterol.* 17, 1519 (2011)). There is a need, therefore, for means, preferably orally or enterally administered means, more preferably dietetic means, for effectively increasing the concentration of butyrate derived after HMO fermentation in the gastro-intestinal tracts of humans, preferably non-infant humans.

SUMMARY OF THE INVENTION

A first aspect of this invention relates to a human milk oligosaccharide (HMO), advantageously a neutral HMO, for use in stimulating the production of butyrate in the gastro-intestinal tract of a non-infant human and obtaining delayed increase in the level of butyrate in the gastro-intestinal tract of said non-infant human.

A second aspect of the invention is a synthetic composition comprising an HMO, advantageously a neutral HMO, for use in stimulating the production of butyrate in the gastro-intestinal tract of a non-infant human and obtaining delayed increase in the level of butyrate in the gastro-intestinal tract of a non-infant human.

The synthetic composition can be a nutritional or pharmaceutical composition.

A third aspect of the invention is a pack for use in increasing the level of butyrate in the gastro-intestinal tract of a non-infant human, the pack comprising at least 14 individual daily doses of an effective amount of an HMO, advantageously a neutral HMO. Preferably, each dose contains about 1 g to about 20 g of the HMO, more preferably about 2 g to about 10 g, for example about 3 g to about 7.5 g. Preferably, the pack comprises at least 21 daily doses, more preferably at least 28 daily doses. The pack can include instructions for use.

The HMO according to the first aspect, the synthetic composition according to the second aspect or the pack according to the third aspect is preferably for use in treating or preventing in the non-infant human:
an enteropathogenic infection,
type 2 diabetes and/or obesity,
impaired gut barrier function,
brain gut disorders such as stress, anxiety and depressive like behaviour,
allergies,
autism like behavior,
colon cancer,
liver damage and/or
an inflammation related to a gastro-intestinal condition.

Preferably, the neutral HMO is a fucosylated HMO, such as 2'-FL, 3-FL or DFL, a non-fucosylated HMO, such as LNnT or LNT, or especially a mixture of both. In especially preferred embodiments, the HMO is a mixture of 2'-FL and DFL or a mixture of i) 2'-FL and/or DFL and ii) LNnT and/or LNT, for example 2'-FL and LNnT or 2'-FL and DFL and LNnT.

A fourth aspect of this invention is a method for increasing the production of butyrate in the gastro-intestinal tract of a non-infant human, the method comprising orally or enterally administering to the non-infant human, preferably for a period of at least 14 days, an effective amount of an HMO, advantageously a neutral HMO. The non-infant human is preferably an irritable bowel syndrome (IBS) patient.

A fifth aspect of this invention is a method for the prophylaxis or treatment of an enteropathogenic infection in a non-infant human, the method comprising orally or enterally administering to the non-infant human, preferably for a period of at least 14 days, an amount of one or more HMOs, advantageously neutral HMOs, effective to increase the production of butyrate in the gastro-intestinal tract of the non-infant human.

A sixth aspect of this invention is a method for the prophylaxis or treatment of a non-infant human having type 2 diabetes and/or obesity, the method comprising orally or enterally administering to the non-infant human, preferably for a period of at least 14 days, an amount of one or more HMOs, advantageously neutral HMOs, effective to increase the production of butyrate, in the gastro-intestinal tract of the non-infant human, preferably, sufficient to improve intestinal permeability and/or increase insulin sensitivity.

A seventh aspect of this invention is a method for the prophylaxis or treatment of a non-infant human having an inflammation related to a gastro-intestinal condition or an allergy, the method comprising orally or enterally administering to the non-infant human, preferably for a period of at least 14 days, an amount of one or more HMOs, advantageously neutral HMOs, effective to increase the production of butyrate, in the gastro-intestinal tract of the non-infant human. The gastro-intestinal condition may be intestinal bowel disease or irritable bowel syndrome; preferably, the amount of the HMO(s) is sufficient to induce an anti-inflammatory immune response.

An eighth aspect of this invention is a method for the prophylaxis or treatment of a non-infant human having a brain gut disorder, the method comprising orally or enterally administering to the non-infant human, preferably for a period of at least 14 days, an amount of one or more HMOs, advantageously neutral HMOs, effective to increase the production of butyrate in the gastro-intestinal tract of the non-infant human. The brain gut disorder may be stress, anxiety and depressive like behaviour.

Preferably, in the fourth to eighth aspects, the non-infant human is administered about 1 g to about 20 g of the HMO per day, more preferably about 2 g to about 10 g, for example about 3 g to about 7.5 g.

A ninth aspect of this invention is a method for increasing the production of butyrate in the gastro-intestinal tract of a non-infant human, the method comprising enterally, preferably orally, administering to the non-infant human:
(a) in a first step for a period of about 14 days:
a first amount of an HMO, preferably a neutral HMO, or
a first amount of a synthetic composition comprising an effective amount of an HMO, preferably a neutral HMO,
wherein the first amount is effective to increase the production of butyrate in the gastro-intestinal tract of the non-infant human, and
(b) in a second step for an additional period:
a second amount of an HMO, preferably a neutral HMO, or
a second amount of a synthetic composition comprising an effective amount of an HMO, preferably a neutral HMO,
wherein the second amount is effective to maintain the production of butyrate in the gastro-intestinal tract of the non-infant human.

Preferably, in the first step, the non-infant human is administered about 2 g to about 20 g of the HMO, more preferably about 3 g to about 10 g, for example about 5 g to about 7.5 g. Further, in the second step, the non-infant human is administered about 1 g to about 10 g of the HMO, more preferably about 2 g to about 7.5 g, for example about 2 g to about 5 g.

Preferably, the HMO(s) is/are administered for at least 21 days.

Preferably, the amount of butyrate in the gastrointestinal tract after administration of the HMO for 14 days is at least 100% greater than the amount before administration; more preferably at least 200% greater.

FIGURES

FIG. 1 presents the absolute values of acetic acid (AA), propionic acid (PA), butyric acid (BA) and total SCFA (total) associated with the 2'-FL treatment in the proximal (PC) and distal (DC) colon reactor. Samples were taken during two control weeks, three treatment weeks and two washout weeks. During each week, three samples (A, B, and C, corresponding to day 1, day 3 and day 5, respectively, in a given week) were collected for metabolic analysis.

DETAILED DESCRIPTION OF THE INVENTION

It has now been surprisingly found by that administration of human milk oligosaccharides (HMOs) to non-infant children and adults, for a period of at least 14 days, preferentially increases the abundance of a *Bifidobacterium longum* and/or *Bifidobacterium bifidum*, in the microbiota of their gastro-intestinal tract and raises the level of butyrate produced in the gastro-intestinal tract. It has been previously reported in WO 2016/138911 that the administration of HMOs to a non-infant human increases the abundance of bifidobacteria of the *B. adolescentis* phylogenetic group, especially *Bifidobacterium adolescentis* and/or *Bifidobacterium pseudocatenulatum*. This increase in the bifidobacteria of the *B. adolescentis* phylogenetic group is temporary and lasts about 14 days. Thereafter, the abundance of *Bifidobacterium longum* and/or *Bifidobacterium bifidum* surprisingly increases. Further, it is surprisingly found that continuous administration of HMO(s) to a non-infant human during about 14 days, i.e. at least once a day during about 14 days, stimulates synthesis of butyrate in the gastro-intestinal tract of said non-infant human raising the level of butyrate up to 2-10 fold, such as 3-5 fold, higher compared to the level of butyrate before the beginning of administration of HMO(s), i.e. 100-1000% higher than the initial level.

Thus, it has been discovered that HMOs, by oral or enteral ingestion, dynamically modulate the non-infant human intestinal microbiota by preferentially promoting the growth of the species of *Bifidobacterium longum* and/or *Bifidobacterium bifidum*, increase the abundance of this/these species in the non-infant human intestine and simultaneously increase (in a time-delayed mode) the production of butyrate in the gastro-intestinal tract of said non-infant human. As an outcome, a more beneficial intestinal microbial community and intestinal environment can be shaped and maintained, and by the increased abundance of a *Bifidobacterium longum* and/or *Bifidobacterium bifidum* and beneficial metabolites like butyrate, pathogenic infections can be inhibited and intestinal and extra-intestinal diseases can be prevented or improved. Further the dietary needs of the non-infant human for butyrate may be addressed.

Herein, the following terms have the following meanings:

"Delayed" or "time-delayed" increase means an increase after a period of about 14 days.

"Non-infant human" or "non-infant" means a human of 3 years of age and older. A non-infant human can be a child, a teenager, an adult or an elderly.

"Human milk oligosaccharide" or "HMO" means a complex carbohydrate found in human breast milk (Urashima et al.: *Milk Oligosaccharides*. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition of the invention may be, but preferably is not, identical with a naturally occurring composition. The synthetic composition typically comprises one or more compounds, advantageously HMOs, that are capable of preferentially increasing the abundance of *Bifidobacterium longum* and/or *Bifidobacterium bifidum*, in the microbiota of the gastro-intestinal tract and increase the production of butyrate in the gastro-intestinal tract of said human, when administered for a period of about 14 days. In some embodiments, the synthetic composition may comprise one or more compounds or components other than HMOs that may have an effect on bifidobacteria of a non-infant human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

"Microbiota", "microflora" and "microbiome" preferably mean a community of living microorganisms that typically inhabits a bodily organ or part, particularly the gastro-intestinal organs of non-infant humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniform is, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a non-infant through the mouth. Accordingly, oral administration is a form of enteral administration.

"Effective amount" means an amount of a composition that provides an HMO in a sufficient amount to render a desired treatment outcome in a non-infant human. An effective amount can be administered in one or more doses to achieve the desired treatment outcome.

"Relative abundance of a *Bifidobacterium longum* and/or *Bifidobacterium bifidum*" preferably means the abundance of a *Bifidobacterium longum* and/or *Bifidobacterium bifidum* relative to other bifidobacteria in the microbiota of the gastro-intestinal tract of non-infant humans.

"Relative growth of a *Bifidobacterium longum* and/or *Bifidobacterium bifidum*" means the growth of a *Bifidobacterium longum* and/or *Bifidobacterium bifidum* relative to other bifidobacteria in the microbiota in the gastro-intestinal tract of non-infant humans.

"*Bifidobacterium* of the *B. adolescentis* phylogenetic group" means a bacterium selected from a group consisting of *Bifidobacterium adolescentis*, *Bifidobacterium angulatum*, *Bifidobacterium catenulatum*, *Bifidobacterium pseudocatenulatum*, *Bifidobacterium kashiwanohense*, *Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)). Preferably a *Bifidobacterium* of the *B. adolescentis* phylogenetic group is *Bifidobacterium adolescentis* and/or *Bifidobacterium pseudocatenulatum*.

"Relative abundance of a *Bifidobacterium* of the *B. adolescentis* phylogenetic group" means the abundance of a *Bifidobacterium* of the *B. adolescentis* phylogenetic group relative to other bifidobacteria in the microbiota of the gastro-intestinal tract of non-infants.

"Relative abundance of *B. adolescentis* and/or *B. pseudocatenulatum*" means the abundance of *B. adolescentis* and/or *B. pseudocatenulatum* relative to other bifidobacteria in the microbiota of the gastro-intestinal tract of non-infants.

"Relative growth of a *Bifidobacterium* of the *B. adolescentis* phylogenetic group" means the growth of a *Bifidobacterium* of the *B. adolescentis* phylogenetic group relative to other bifidobacteria in the microbiota in the gastro-intestinal tract of non-infants.

"Relative growth of *B. adolescentis* and/or *B. pseudocatenulatum*" means the growth of *B. adolescentis* and/or *B. pseudocatenulatum* relative to other bifidobacteria in the microbiota in the gastro-intestinal tract of non-infants.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

In accordance with this invention, it has been discovered that an HMO, preferably a neutral HMO, preferably a fucosylated HMO, such as 2'-FL or a mixture of two or more neutral HMOs, preferably a mixture comprising at least one fucosylated and at least one non-fucosylated HMO, such as a mixture of 2'-FL and LNnT, can stimulate the production of butyrate in the gastro-intestinal tract of non-infant humans in a time-delayed mode, when administered to said non-infant humans for about 14 days. For this reason, an HMO can be used for increasing the level of butyrate produced in the gastro-intestinal tract of non-infant humans and available for absorption by the non-infant human. Accordingly, an HMO can be used for addressing the dietary needs of the non-infant human for butyrate, treating or preventing viral and/or bacterial infections (especially enteropathogenic infections), reducing inflammation associated with gastro-intestinal diseases (especially IBS and IBD), allergies and gut-brain disorders and extra-intestinal diseases (especially obesity and type 2 diabetes, autism, colon cancer and liver damage) in non-infant humans.

Accordingly, the first aspect of the invention relates to an HMO, advantageously a neutral HMO, preferably, a fucosylated HMO, for use for the delayed increase in the level of butyrate in the gastro-intestinal tract of non-infant humans. The HMO consequently may be used for treating and/or preventing viral and/or bacterial infections (especially enteropathogenic infections), inflammation associated with gastro-intestinal diseases (especially IBS and IBD), allergies and gut-brain disorders and extra-intestinal diseases (especially obesity and type 2 diabetes, autism, colon cancer and liver damage) in non-infant humans.

The neutral HMO is in one embodiment one or more fucosylated HMOs, in another embodiment, the HMO is one or more non-fucosylated HMOs. In one embodiment, the neutral HMO is a mixture neutral HMOs, preferably a mixture comprising or consisting of a fucosylated and a non-fucosylated neutral HMO. Particularly, the mixture contains or consists of one or more fucosylated neutral HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, preferably, at least 2'-FL, and a non-fucosylated neutral HMO selected from the list consisting of LNT, LNnT, LNH, LNnH, pLNH and pLNnH, e.g. LNnT. In some preferred embodiment, the mixture contains or consists of a fucosylated neutral HMO selected from the list consisting of 2'-FL, 3-FL and DFL, and a non-fucosylated neutral HMO selected from the list consisting of LNT and LNnT, advantageously the mixture comprises or consists of i) 2'-FL and/or DFL and ii) LNnT and/or LNT (meaning that the mixture comprises or consists of at least one of 2'-FL and DFL, and at least one of LNnT and LNT). The mixture can also be that containing or consisting of 2'-FL and DFL.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2011/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The second aspect of this invention is a synthetic composition comprising a neutral HMO as disclosed above in the first aspect, for use in the delayed increase in the level of butyrate in the gastro-intestinal tract of a non-infant. The HMO consequently may be used for treating and/or preventing viral and/or bacterial infections (especially enteropathogenic infections), intestinal inflammation associated with gastro-intestinal diseases (especially IBS and IBD), allergies and gut-brain disorders and extra-intestinal diseases (especially obesity and type 2 diabetes, autism, colon cancer and liver damage).

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the gastro-intestinal (GI) tract or stomach.

The pharmaceutical compositions can also include therapeutic agents such as antiviral agents, antibiotics, probiotics, analgesics, and anti-inflammatory agents. The proper dosage of these compositions for a non-infant human can be determined in a conventional manner, based upon factors such immune status, body weight and age. In some cases, the dosage will be at a concentration similar to that found for the HMO, advantageously a neutral HMO, in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. The total amount of all HMOs will generally be about 1 g to about 20 g, more preferably about 2 g to about 10 g, for example about 3 g to about 7.5 g. Appropriate dose regimes can be determined by conventional methods.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for non-infants with inflamed GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition. Preferably the nutritional composition is free from lactose. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for non-infants with inflamed GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for non-infants having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. The composition can be fed to a non-infant via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition, preferably the nutritional composition, can also be in a unit dosage form such as a capsule, tablet or sachet/stick pack. For example, the nutritional composition can be in a tablet form or powder form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet/stick pack form, can also include various nutrients including macronutrients.

The HMO or synthetic composition can be presented in the form of a pack comprising at least 14 individual daily doses of an effective amount of the HMO. The daily doses are preferably in sachet/stick pack form but may be in any suitable form. Each dose preferably contains about 1 g to about 20 g of the HMO, more preferably about 2 g to about 10 g, for example about 3 g to about 7.5 g. Preferably the pack comprises at least 21 daily doses, more preferably at least 28 daily doses. Most suitable packs contain sufficient for 4 weeks or a full month. The pack can include instructions for use.

A first target group of this invention includes non-infants in need of butyrate. Their ingestion of one or more HMOs as describe above for a period of at least about 14 days will stimulate the production of butyrate in their gastro-intestinal tract and increase level of butyrate in the gastro-intestinal tract to up to 100-1000% (i.e. 2-11 fold) after 14 days from the beginning of ingestion. The non-infant may be an irritable bowel syndrome patient.

A second target group of this invention includes non-infants with an enteropathogenic infection. Their ingestion of one or more HMOs as describe above for a period of at least about 14 days will stimulate the production of butyrate in their gastro-intestinal tract and increase level of butyrate in the gastro-intestinal tract to up to 100-1000% (i.e. 2-11 fold) after 14 days from the beginning of ingestion, and, as a result, induce a favourable immune response against the enteropathogenic microorganism, inhibiting or treating infection.

A third target group for this invention includes obese non-infants, and/or lean or obese non-infants diagnosed with type 2 diabetes. Their ingestion of one or more HMOs as described above, for a period of at least 14 days will stimulate the production of butyrate in their gastro-intestinal tract and increase level of butyrate in the gastro-intestinal tract to up to 100-1000% (i.e. 2-11 fold) after 14 days from the beginning of ingestion, and as a result, improves intestinal permeability and/or increases insulin sensitivity, hence reducing the pathological conditions of type 2 diabetes and/or obesity.

A fourth target group for this invention includes non-infants diagnosed with intestinal inflammation associated with gastro-intestinal diseases such as IBD and IBS and immune-related conditions such as allergies. Their ingestion of one or more HMOs as described above, for a period of at least about 14 days will stimulate the production of butyrate in their gastro-intestinal tract and increase level of butyrate in the gastro-intestinal tract to up to 100-1000% (i.e. 2-11 fold) after 14 days from the beginning of ingestion, and as a result, contributes to immunomodulation by inducing an anti-inflammatory immune response, hence improving symptoms.

The fourth aspect of this invention provides a method for increasing the level of butyrate in the gastro-intestinal tract of a non-infant, the method comprising enterally, preferably orally, administering to the non-infant human for a period of at least about 14 days:
an effective amount of one or more HMOs, or
a synthetic composition comprising an effective amount of one or more HMOs.

The fifth aspect of this invention is a method for the prophylaxis or treatment of an enteropathogenic infection in a non-infant, the method comprising enterally, preferably orally, administering to the non-infant human for a period of at least 14 days:
an amount of one or more HMOs, or
a synthetic composition comprising an amount of one or more HMOs,
effective to increase the level of butyrate in the gastro-intestinal tract of said human up to 100% or more, compared to the butyrate level before initiating the administration.

The sixth aspect of this invention provides a method for the prophylaxis or treatment of a non-infant in an obese state and/or having type 2 diabetes, the method comprising enterally, preferably orally, administering to the non-infant human for a period of at least 14 days:
an amount of one or more HMOs, or
a synthetic composition comprising an amount of one or more HMOs,
effective to increase the level of butyrate in the gastro-intestinal tract of said human up to 100% or more, compared to the butyrate level before initiating the administration.

The seventh aspect of this invention provides a method for the prophylaxis or treatment of a non-infant human having an inflammation related gastro-intestinal condition or an immune related condition such as allergy, the method comprising enterally, preferably orally, administering to the non-infant human for a period of at least 14 days:
an amount of one or more HMOs, or
a synthetic composition comprising an amount of one or more HMOs,
effective to increase the level of butyrate in the gastro-intestinal tract of said human up to 100% or more, compared to the butyrate level before initiating the administration. The gastro-intestinal condition is preferably intestinal bowel disease or irritable bowel syndrome.

The eighth aspect of this invention is a method for the prophylaxis or treatment of a non-infant human having a gut-brain disorder, for example stress, anxiety or depressive like behaviour, or autism, the method comprising enterally, preferably orally, administering to the non-infant human for a period of at least 14 days:
an amount of one or more HMOs, or
a synthetic composition comprising an amount of one or more HMOs,
effective to increase the level of butyrate in the gastro-intestinal tract of said human up to 100% or more, compared to the butyrate level before initiating the administration.

The ninth aspect of this invention is method for stimulating the production of butyrate in the gastro-intestinal tract of a non-infant human, the method comprising enterally, preferably orally, administering to the non-infant human:
(a) in a first step for a period of about 14 days:
a first amount of one or more HMOs, or
a first amount of synthetic composition comprising an effective amount one or more HMOs,
to increase the level of butyrate in the gastro-intestinal tract of the non-infant human to the level up to 100% or more, such as 200-500% higher, compared to the butyrate level before the initiation of administration, and
(b) in a second step for an additional period:
a second amount of one or more HMOs, or
a second amount of a synthetic composition comprising an effective amount one or more HMOs,
to maintain the level of butyrate production in the gastro-intestinal tract of the non-infant human achieved after the 14-day administration of the first amount of the HMO or the HMO composition.

In the fourth to ninth aspects of therapeutic and prophylactic treatment of the invention, the HMO is as described above.

For stimulating the butyrate production in the gastro-intestinal tract of a non-infant human, the amount of HMO(s) required to be administered will vary depending upon factors such as the need for butyrate and the risk and severity of the obesity, type 2 diabetes, the inflammatory gastrointestinal condition, the allergy, the gut brain disorder or the enteropathogenic infection, age, the form of the composition, and other medications being administered. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, body weight and/or condition, the severity of the of type 2 diabetes, the inflammatory gastrointestinal condition or the enteropathogenic infection, being treated or prevented, other ailments and/or diseases, the incidence and/or severity of side effects and the manner of administration. Appropriate dose ranges may be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day, which dose corresponds to the first effective amount of HMO(s)). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day, which dose corresponds to the second effective amount of HMO(s)).

Whilst the invention has been described with reference to a preferred embodiment, it will be appreciated that various modifications are possible within the scope of the invention.

EXAMPLES

The working example described herein are for illustration purposes only and should not be considered as limiting.

Example 1

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture of 2'-FL and LNnT, h) 10 g of a 2:1 mixture of 2'-FL and LNnT, and i) 5 g of a 2:1 mixture of 2'-FL and LNnT for 4 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 4 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

After 2 weeks, each participant has a visit with the medical team. Faecal samples and blood samples are collected. The faecal samples are stored at −80° C. until analysis. Equipment for new samples are distributed. Subjects are reminded not to change their usual diet during the study.

After 4 weeks, each participant has an exit visit with the medical team. Faecal samples and blood samples are collected. The faecal samples are stored at −80° C. until analysis.

Blood samples are analysed simultaneously in a multiplexing format on an electrochemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al., *Nucleic Acids Res.* 41, e1 (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013)) is used for bioinformatical analysis of the sequence data.

To assess the *Bifidobacterium* community, ITS profiling of DNA samples is performed.

The results from the profiling of the *Bifidobacterium* community shows that, for the first 2 weeks, the abundance of *B. adolescentis* increases when consuming a single HMO, where the abundance of *B. psedocatenulatum* increases when consuming a mix of two HMOs. Both *B. adolescentis* and *B. psedocatenulatum* are members of the *B. adolescentis* phylogenetic group. At 4 weeks, the abundance of members of the *B. adolescentis* phylogenetic group reduce while the abundance of *Bifidobacterium longum* and/or *Bifidobacterium bifidum* increase. It can be seen that oral ingestion of the HMOs for more than 14 days clearly increases the abundance of *Bifidobacterium longum* and/or *Bifidobacterium bifidum* in the microbiota of healthy adults, as well as their relative abundance compared to the totality of other *Bifidobacterium* species. Further butyrate production increases after 14 days.

Example 2

The impact of the HMOs on microbiota was investigated in the M-SHIME® (M-TripleSHIME®) in vitro gastrointestinal model (Prodigest). The typical reactor setup of the M-TripleSHIME® consisted of a succession of four reactors simulating the different parts of the human gastrointestinal tract. The first two reactors were of the fill-and-draw principle to simulate different steps in food uptake and digestion, with peristaltic pumps adding a defined amount of SHIME feed (140 ml 3×/day) and pancreatic and bile liquid (60 ml 3×/day), respectively to the stomach and small intestine compartment and emptying the respective reactors after specified intervals. The last two compartments were continuously stirred reactors with constant volume and pH control. The retention time and pH of the different vessels were chosen to resemble in vivo conditions in the different parts of the colon. The proximal colon was set to pH 5.4-5.6 and retention time=12 h, and the distal colon was set to pH 6.0-6.5 and retention time=20 h. 2'-FL, LNnT or Mix (2'-FL:LNnT in 4:1 weight ratio) was added to the SHIME feed in a concentration that equals 10 gram per day.

Upon inoculation with faecal microbiota, these reactors simulated the ascending, transverse and descending colon. After a two-week adaptation of the microbial communities in the different regions of the colon, a representative microbial community was established in the three colon compartments, which differs both in composition and functionality in the different colon regions.

Further, porcine mucin was included in the reactors simulating the colon to take into account the colonisation of the mucous layer. Thus, the M-SHIME® permitted culturing both the luminal and mucous-associated microbial community over periods of several weeks.

The M-SHIME® was run in four stages:
1. Stabilisation: After inoculation of the reactors with a fresh faecal sample taken from a healthy adult, a two-week stabilisation period allowed the microbial community to differentiate in the different reactors depending on the local environmental conditions. During this period the basic nutritional matrix was provided to support the maximum diversity of the gut microbiota originally present in the faecal inoculum.
2. Control: During this two-week period, a standard nutrient matrix was dosed into the model for a period of 14 days. The baseline microbial community composition and activity in the different reactors was determined by analysis of samples and was used as a reference.
3. Treatment: The SHIME system was operated under normal conditions for 3 weeks, but with the standard nutrient matrix supplemented with the HMOs. The HMOs tested were 2'-FL, LNnT and a 4:1 mix of 2'-FL and LNnT.
4. Washout: During this two-week period, the SHIME system is again run with the standard nutrient matrix only.

Samples of the liquids in each reactor were collected regularly (the first, third and fifth day in a week, correspond to A, B, C, respectively, in FIG. 1) and were analysed for microbial metabolites and the composition of the resident microbial community. In particular, the bifidobacteria composition was analysed using ITS profiling.

The results from the fermentation system showed that HMOs impacted the base-acid consumption meaning that HMOs were fermented both in the proximal colon and, to a lesser extent, the distal colon. The bacterial metabolite analysis showed that HMO treatment induced an immediate increase in total SCFA production in both colon regions, mainly due to increase in the production of acetate and propionate. During the third week of HMO treatment, butyrate was increased. This was associated with a decrease in acetate (FIG. 1).

The profiling of the *Bifidobacterium* community showed that, for the first 2 weeks, the abundance of *B. adolescentis* increased when consuming HMOs. However, by week 3, the relative abundance of members of the *B. adolescentis* phylogenetic group reduced while the abundance and relative abundance of *Bifidobacterium longum* and/or *Bifidobacterium bifidum* increased.

It can be seen that feeding the M-SHIME with HMOs impact the production of SCFA and treatment for more than 14 days increases the concentration of butyrate in both colon regions.

The invention claimed is:
1. A method comprising:
   selecting a non-infant human not having used probiotic supplements for at least three months;
   selecting an effective amount of one or more synthetic neutral human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human;
   increasing the relative abundance of *Bifidobacterium adolescentis* in the gastrointestinal microbiota of the non-infant human by enterally administering to the non-infant human for a first treatment period of at least 14 days, a daily dose of from about 1 g to about 15 g of the chosen one or more HMOs;
   increasing in a time-delayed increase a level of butyrate produced in the gastrointestinal tract of the non-infant human relative to the level of butyrate produced before the first treatment period; and
   reducing the likelihood of the non-infant human experiencing at least one condition associated with a gastrointestinal disorder by the administration.
2. The method of claim 1, wherein the at least one condition associated with the gastrointestinal disorder is selected from the group consisting of impaired gut barrier function, gut-related inflammation, autism-like behavior, a brain-gut disorder, and combinations thereof.
3. The method of claim 1, wherein the chosen one or more HMOs comprise 2'-FL in an amount comprising at least two thirds of the daily dose.
4. The method of claim 1, wherein the increased level of butyrate produced during the first treatment period is selected from at least 100%, at least 200%, at least 300%, and at least 500%.
5. The method of claim 1,
   further comprising increasing the relative abundance of a second group of one or more species of adult-type bifidobacteria in the gastrointestinal microbiota of the non-infant human by the administration.
6. The method of claim 5, wherein the second group of one or more species of adult-type bifidobacteria is selected from *Bifidobacterium longum* and *Bifidobacterium bifidum*.
7. The method of claim 1, wherein the one or more synthetic neutral HMOs comprise a mixture of at least one fucosylated HMO and at least one non-fucosylated HMO.
8. The method of claim 1, wherein the daily dose of the chosen one or more HMOs is from about 2 g to about 10 g.
9. The method of claim 1, wherein the chosen one or more HMOs comprise a mixture of:
   at least one fucosylated HMO selected from 2'-FL, 3-FL, LNFP-I, and DFL; and
   at least one non-fucosylated HMO selected from LNT and LNnT.
10. A method comprising:
   selecting a non-infant human not having used probiotic supplements for at least three months;
   selecting an effective amount of one or more neutral human milk oligosaccharides (HMOs) chosen from the group consisting of 2'-fucosyllactose (2'-FL), 3-fuco- syllactose(3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human;

increasing the relative abundance of *Bifidobacterium adolescentis* in the gastrointestinal microbiota of the non-infant human by enterally administering to the non-infant human for a first treatment period of at least 14 days, a daily dose of from about 1 g to about 15 g of the chosen one or more HMOs;

increasing in a time-delayed increase a level of butyrate produced in the gastrointestinal tract of the non-infant human in at least a portion of the first treatment period relative to the level of butyrate produced before the first treatment period;

enterally administering a lower dosage of the chosen one or more HMOs to the non-infant human for a second treatment period;

maintaining in the non-infant human during the second treatment period, an increased level of butyrate produced in the gastrointestinal tract of the non-infant human relative to the level of butyrate produced before the first treatment period; and reducing the likelihood of non-infant human experiencing at least one condition associated with a gastrointestinal disorder by the administration.

11. The method of claim 10, wherein the at least one condition associated with the gastrointestinal disorder is selected from the group consisting of impaired gut barrier function, gut-related inflammation, autism-like behavior, a brain-gut disorder, and combinations thereof.

12. The method of claim 10, wherein the chosen one or more HMOs comprise 2'-FL in an amount comprising at least two thirds of the daily dose.

13. The method of claim 10, further comprising increasing the relative abundance of a second group of one or more adult-type species of bifidobacteria in the gastrointestinal microbiota of the non-infant human during the second treatment period by the administration.

14. The method of claim 13, wherein the second group of one or more species of adult-type bifidobacteria is selected from *Bifidobacterium longum* and *Bifidobacterium bifidum*.

15. The method of claim 10, wherein the sum of the first treatment period and the second treatment period is at least 21 days.

16. The method of claim 10, wherein the daily dose of the chosen one or more HMOs is from about 2 g to about 10 g.

17. A method comprising:

selecting a non-infant human not having used probiotic supplements for at least three months;

selecting an effective amount of one or more neutral human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human; and enterally administering to the non-infant human for a first treatment period of at least 14 days, a daily dose of from about 1 g to about 15 g of the chosen one or more HMOs, wherein the selected amount of the chosen one or more HMOs administered is effective to:

increase in the gastrointestinal microbiota of the non-infant human during the first treatment period an abundance of *Bifidobacterium adolescentis* relative to an abundance of bacteria other than bifidobacteria in the gastrointestinal microbiota of the non-infant human;

increase a level of acetate produced during the first treatment period and increase a level of butyrate produced in a time-delayed increase in the gastrointestinal tract of the non-infant human, relative to the levels of acetate and butyrate produced before the first treatment period; and reduce the likelihood of non-infant human experiencing at least one condition associated with a gastrointestinal disorder by the administration.

18. The method of claim 17, wherein the at least one condition associated with the gastrointestinal disorder is selected from the group consisting of impaired gut barrier function, gut-related inflammation, autism-like behavior, a brain-gut disorder, and combinations thereof.

19. The method of claim 17, wherein the increased level of butyrate produced during the first treatment period is selected from at least 100%, at least 200%, at least 300%, and at least 500%.

* * * * *